United States Patent [19]

Taylor, Jr. et al.

[11] Patent Number: 4,508,724

[45] Date of Patent: Apr. 2, 1985

[54] ARYLOXYMETHYLPYRROLIDINOLS AND PIPERIDINOLS HAVING ANTIDEPRESSANT, ANTIARRHYTHMIC OR HYPOTENSIVE ACTIVITY

[75] Inventors: Chandler R. Taylor, Jr., Mechanicsville; Harold F. Stauffer, Jr., Midlothian, both of Va.

[73] Assignee: A. H. Robins Company, Inc., Richmond, Va.

[21] Appl. No.: 576,904

[22] Filed: Feb. 3, 1984

[51] Int. Cl.$^3$ .................. C07D 211/48; C07D 207/12; A61K 31/40; A61K 31/445

[52] U.S. Cl. ...................... 514/317; 514/319; 514/424; 546/206; 546/216; 546/222; 548/556

[58] Field of Search .................... 546/216, 222, 206; 548/556; 424/267, 274

[56] References Cited

PUBLICATIONS

Chemical Abstracts, vol. 73, (1970), 66442j.

Chemical Abstracts, vol. 79, (1973), 126228e.

Shiro Morosawa, Bull. Chem. Soc. Japan, (1960), vol. 33(5), pp. 575–578.

Primary Examiner—Norma S. Milestone

[57] ABSTRACT

Novel aryloxymethylpyrrolidinols and piperidinols are provided of the formula:

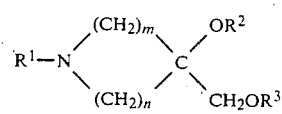

wherein $R^1$ is hydrogen, loweralkyl and phenylloweralkyl; $R^2$ is hydrogen, loweralkyl and acyl; $R^3$ is phenyl, naphthyl, 4-indanyl and 5-indanyl; m is 2 or 3 and n is 1 or 2; and the pharmaceutically acceptable salts thereof, having antiarrhythmic, antidepressant and antihypertensive activity.

49 Claims, No Drawings

ARYLOXYMETHYLPYRROLIDINOLS AND PIPERIDINOLS HAVING ANTIDEPRESSANT, ANTIARRHYTHMIC OR HYPOTENSIVE ACTIVITY

BACKGROUND OF THE INVENTION

1. Field of Invention

The present invention relates to certain aryloxymethylpyrrolidinols and piperidinols and pharmaceutically acceptable salts thereof, compositions containing the same and methods of use thereof to control various physiological abnormalities in humans and other mammals.

2. Information Disclosure Statement

Various related compounds are known in the art. For example, compounds of the formula:

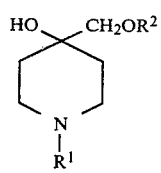

are known where $R^1$ is hydrogen or phenylalkyl and $R^2$ is hydrogen or alkyl (Bull. Chem. Soc. Jap., 33(5), pp. 575–8, 1960).

Compounds of the formula:

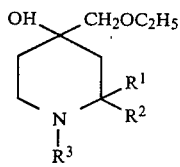

are known where $R^3$ is hydrogen, phenylalkyl or alkyl (A. S. Noravyan et al, *Dokl. Vses. Konf. Khim. Atsetilena*, 4th 1972, 1, pp. 348–52, from *Ref. Zh., Khim.*, 1973, abst. No. 6Zh282 (Chem. Abst. 79, 126228e). Also known are compounds of the formula:

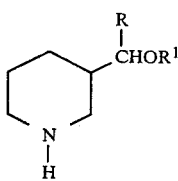

where R is hydrogen, lower alkyl and phenyl and $R^1$ is substituted phenyl and phenyl (CA73:66442j; French Demande 2,010,615). French Pat. No. 1,515,848 discloses compounds of the formula:

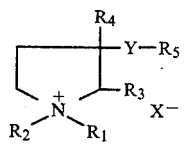

wherein $R^1$, $R^3$ and $R^4$ are hydrogen and lower alkyl, $R^2$ is aralkyl or thenyl; $R^5$ is hydrogen, alkanoyl and aroyl; and Y is oxygen or sulfur, French Pat. No. 2,136,903 discloses compounds of the formula:

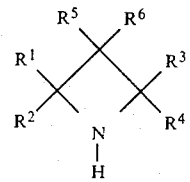

wherein $R^1$, $R^2$, $R^3$ and $R^4$ are alkyl; $R^5$ is hydrogen, hydroxy, benzoyloxy, —$CH_2OH$; and $R^6$ is hydroxy, benzoyloxy.

Compounds of the formula:

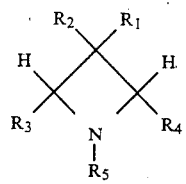

are also known wherein $R_1$ is a free, esterified or etherified hydroxy group, $R_2$ is aryl, alkyl, cycloalkyl, alkoxy or halogen, $R_3$ and $R_4$ are hydroen, alkyl, cycloalkyl, or aryl; and $R_5$ is alkyl, cycloalkyl, alkenyl, cycloalkenyl or aralkyl.

Furthermore, compounds of the formula:

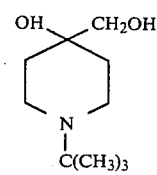

are also known.

SUMMARY OF THE INVENTION

The present invention is directed to aryloxymethylpyrrolidinols and piperidinols, compositions containing the same as active ingredients and methods of use thereof in controlling physiological abnormalities such as cardiac arrhythmias, hypertension or depression, said compounds having the formula:

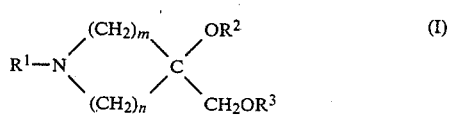

wherein $R^1$ is hydrogen, loweralkyl or phenyl loweralkyl; $R^2$ is hydrogen, loweralkyl or acyl; $R^3$ is phenyl, 1-naphthyl, 2-naphthyl, 1H-2,3-dihydroinden-4-yl and 1H-2,3-dihydroinden-5-yl; m is 2 or 3, and n is 1 or 2 with the proviso that m is never 3 when n is 2.

The pharmaceutically acceptable salts of the above compounds are also within the scope of the present invention.

DETAILED DESCRIPTION OF THE INVENTION

The compounds described hereinafter and represented by Formula I have been shown by acceptable pharmacological procedures to have utility as physiologically active agents. Such compounds are effective as antiarrhythmic agents therapeutically applicable in the treatment of cardiac arrhythmias and hypertension and possess antidepressant activity.

In the definitions of the symbols as they appear in Formula I and elsewhere in this specification, the terms below shall have the noted significance.

The term "lower alkyl" as used herein includes straight and branched chain radicals of from 1 to 8 carbon atoms inclusive. Examples of lower alkyl radicals suitable for use in the present invention include methyl, ethyl, propyl, n-butyl, isopropyl, isobutyl, amyl, isoamyl, hexyl, heptyl, octyl, isooctyl, etc.

The term "phenyl loweralkyl" as used herein includes groups such as benzyl, phenethyl, 1-phenylethyl, phenpropyl, etc. wherein "loweralkyl" is as defined above.

The term "phenyl" includes the unsubstituted phenyl radical, the substituted phenyl radical and the disubstituted phenyl radical. Among the suitable substituted and disubstituted phenyl radicals are those which are substituted by any radical or radicals which are not reactive or otherwise interfering under the conditions of reaction in preparing the desired compound, such as, for example, lower alkyl, lower alkoxy, trifluoromethyl, acetyl, acetylamino and halo. The substituted phenyl radicals have preferably one or two substituents such as those given above and, furthermore, the substituents can be in various available positions of the phenyl nucleus and, when more than one substituent is present, can be the same or different and can be in various combinations relative to each other. The lower alkyl and alkoxy substituents each have preferably from 1 to 4 carbon atoms which can be arranged either as straight or branched chains. A total of 9 carbon atoms in all ring substituents, making a total of 15 carbon atoms in the radical, is the preferred maximum.

The compounds of the present invention may be conveniently employed in the form of pharmaceutically acceptable acid addition salts and quaternary salts. Appropriate acid addition salts are those derived from mineral acids such as hydrochloric, hydrobromic, sulfuric, and phosphoric; and organic acids such as acetic, citric, lactic, maleic, oxalic, fumaric, cyclohexylsulfamic and tartaric. The preferred acid addition salt is the hydrochloride. The salts are conveniently prepared by reaction of the basic compounds with the selected acid, either or both of which may be in the form of ether, alcohol, or acetone solutions. Suitable quaternary salts include the loweralkyl halides and loweralkyl sulfates.

The antiarrhythmic activity of certain of the novel compounds of the present invention was demonstrated using the following procedure. Adult mongrel dogs of either sex weighing from 8 to 14 kg were used under barbituate anesthetic. A Grass Model 7 polygraph was used for recording femoral arterial blood pressure (Statham P23Ac Transducer) and the electrocardio (Grass 7p4 Preamplifier). Ouabian was given intravenously in an initial dose of 40 μg/kg, in a second dose of 20 μg/kg given 30 minutes later and in subsequent doses of 10 μg/kg which are repeated at 15 minute intervals for producing cardiac arrhythmias that persisted for at least 15 minutes. When the arrhythmias were established, the test compounds were administered by infusion (Harbard Model 942 Infusion Pump) into a femoral vein at a rate of 1 mg/kg/min. Concentrations of compounds were adjusted according to the weight of the dog to allow a volume infusion of 1 mg/kg/min. Compounds that are considered to be active as antiarrhythmic agents elicit revision of the arrhythmia to sinus rhythm for at least 30 minutes.

In accordance with the above tests and evaluation procedures, it was determined that the following representative compounds of the present invention corrected ouabain-induced arrhythmias in anesthetized dogs: 4-phenoxymethyl-1-phenylmethyl-4-piperidinol hydrobromide (corrective dose of 3.5 mg/kg, i.v.); 3-[2-ethoxyphenoxy)methyl]-3-pyrrolidinol (corrective dose of 3.0 mg/kg, i.v.); 3-[(1-naphthalenyloxy)methyl]-1-phenylmethyl-3-pyrrolidinol (corrrective dose of 2.5 mg/kg, i.v.); 3-[(1-naphthalenyloxy)methyl]-3-pyrrolidinol hydrochloride (corrective dose of 8.0 mg/kg, i.v.); 3-ethoxy-3-[(2-ethoxyphenoxy)methyl]pyrrolidine hydrochloride (corrective dose of 6.0 mg/kg, i.v.); and 4-[[(1H-2,3-dihydroinden-4-yl)oxy]methyl]-1-phenylmethyl-4-piperidinol hydrochloride (corrective dose of 2.0 mg/kg, i.v.).

For the purpose of testing hypotensive activity, spontaneously hypertensive rats were used for determining the blood pressure lowering activity of the test compounds. Indwelling arterial catheters were placed either in the caudol artery or the abdominal aorta. These indwelling catheters were used for direct measurements of blood pressure from conscious animals using a Statham pressure transducer and recorded by a Grass polygraph.

In accordance with the above test, it was determined that the following representative compounds exhibited hypotensive activity: 4-phenoxymethyl-4-piperidinol hydrochloride; 3-[(2-ethoxyphenoxy)methyl]-3-pyrrolidinol; 3-[(1-naphthalenyloxy)methyl]-3-pyrrolidinol hydrochloride; 3-ethoxy-3-[(2-ethoxyphenoxy)methyl]-pyrrolidine hydrochloride; 4-[[[1H-2,3-dihydroinden-4-yl]oxy]methyl]-1-phenylmethyl-4-piperidinol hydrochloride; 4-[[[1H-2,3-dihydroinden-4-yl]oxy]methyl]-4-piperidinol hydrochloride; 1-methyl-3-(phenoxymethyl)-3-piperidinol monohydrochloride; 3-(phenoxymethyl)-3-piperidinol monohydrochloride; 3-[[(1H-2,3-dihydroinden-4-yl)oxy]methyl]-1-phenylmethyl-3-pyrrolidinol; and 3-[[(1H-2,3-dihydroinden-4-yl)oxy]methyl]-3-pyrrolidinol hydrochloride.

Antidepressant agents block many of the behavioral and physiological effects of tetrabenzine and reserpine, such as motor depression, hypothermia, and ptosis. Tetrabenazine is chemically related to reserpine which produces depression in humans. See Davies, E. D., *Depression*, Cambridge University Press, N.Y., 1964. Tetrabenazine is generally more widely used as a tool for screening potential anti-depressant drugs.

For the purpose of testing the antidepressant activity of the compounds of the present invention, five adult female mice (ICR-DUB strain) are given 20 mg/kg IP of the test compound thirty minutes prior to the administration of a ptotic dose (32 mg/kg IP) of tetrabenazine (as a methane sulfonate salt). Thirty minutes later the presence or absence of complete eyelid closure (ptosis) is assessed in each animal.

For compounds that produced blockage of ptosis in all animals, an $ED_{50}$ value is obtained using a minimum of three geometrically spaced dosages with five mice/dose. Protective $ED_{50}$ values are determined by probit analysis with 95 percent confidence limits and slope functions calculated by the method of Litchfield and Wilcoxon, *J. Pharm. Exp. Ther.*, 96, pp. 99–113, 1949.

In accordance with the above antidepressant test and evaluation procedures, 3-[2-(ethoxyphenoxy)methyl]-3-methoxypyrrolidine fumarate has an $ED_{50}$ mg/kg (IP)

of 6.5, and 3-(phenoxymethyl)-1-(phenylmethyl)-3-piperidinol monohydrochloride has an ED$_{50}$ mg/kg (IP) of 4.9.

Certain of the quaternary salts; namely, the benzyl derivatives, in addition to being active pharmacological agents are also chemical intermediates and, as will be recognized, many of the other active agents are chemical intermediates.

GENERAL PREPARATION

Preparation of the Starting Epoxide

Preparation of starting epoxide compounds is represented by the following equation:

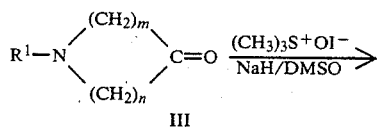

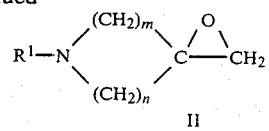

A solution of a ketone as shown above wherein $R^1$ is preferably benzyl (but may also be a lower alkyl, phenyl or other phenyl-loweralkyl is dimethyl sulfoxide is added to a solution of sodium hydride and trimethylsulfoxonium iodide according to the procedure of Corey and Chaykovsky, *J. Amer. Chem. Soc.*, 87 (6), pp. 1353–64, 1965. The reaction is typically worked up by diluting the reaction mixture with water and extracting the epoxide product into ether. The intermediate epoxides may be used crude or distilled under high vacuum.

Preparation of Active Agents and Chemical Intermediates

Active agents of Formula I (and chemical intermediates) may be prepared as outlined in the diagram of Chart I.

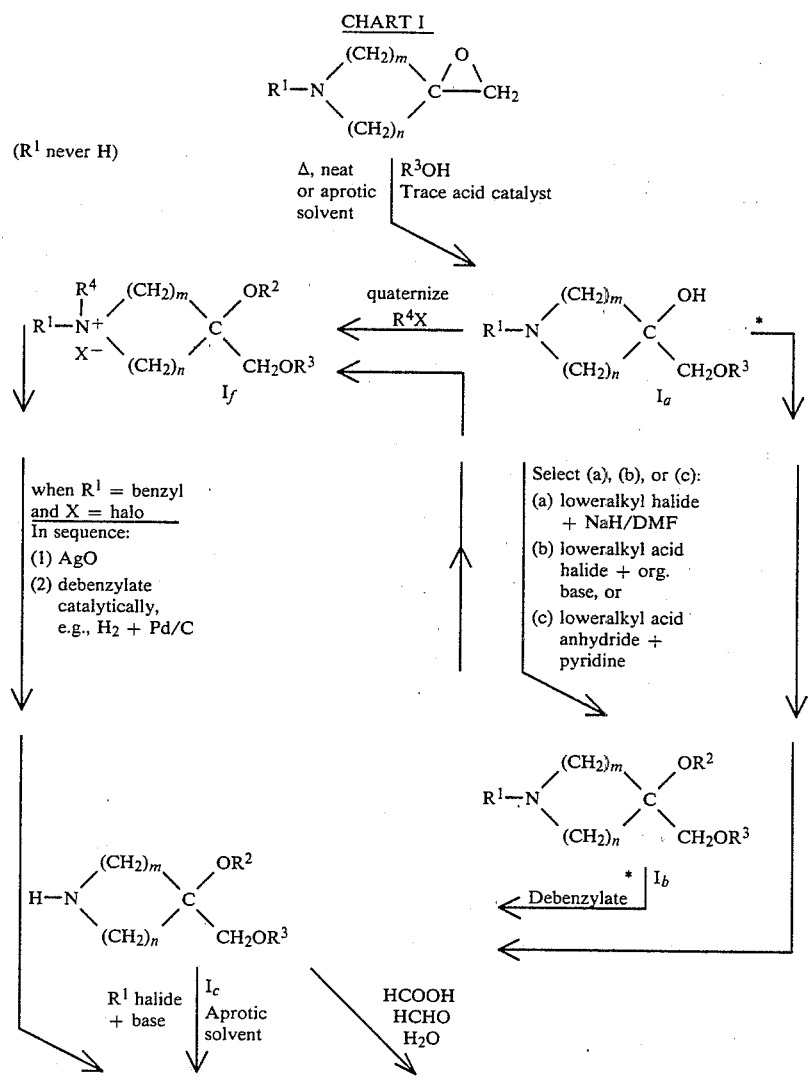

CHART I
-continued

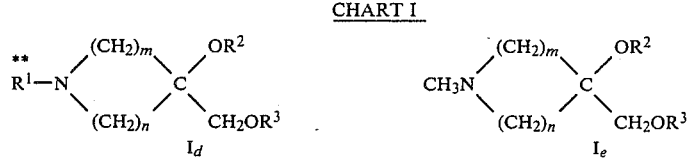

Footnotes:
*When R¹ is benzyl, the debenzylation step may optionally be carried out.
**R¹ other than benzyl.

Alternatively, compounds of Formula I wherein R¹ is methyl and R² is hydrogen or loweralkyl may be prepared as outlined in Chart II.

CHART II

When starting R² = H and R¹ is H or benzyl.

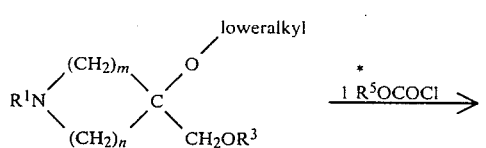

When starting R² = loweralkyl and R¹ is H or benzyl.

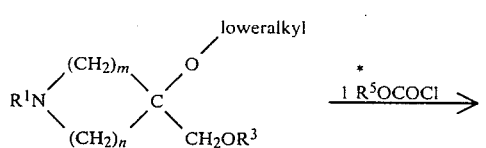

-continued
CHART II

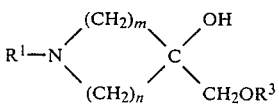

Footnote:
*R⁵ is selected from —CH₃, —C₂H₅, C₆H₅, C₆H₅CH₂, etc.; end product always has R¹ = CH₃.

Compounds of Formulas $I_a$ and $I_b$ are all encompassed by Formula I.

In general, the process of preparing the novel compounds of Formula I of this invention is comprised of and encompassed by the following steps:

Step 1—reacting a compound of the formula wherein R¹ is loweralkyl, phenylloweralkyl or phenyl, preferably benzyl, and m and n are as defined above with a compound having the formula

R³OH wherein R³ is as defined above together with a trace of acidic catalyst to give a compound of the formula wherein R¹, R³, m and n have the starting values.

Step 2—when required, reacting a compound prepared in Step 1 with an alkylating or acylating agent selected from the following:
  (a) loweralkyl halide and sodium hydride (in, e.g., DMF),
  (b) loweralkyl acid halide and organic base, (c) loweralkyl acid anhydride to give a compound of the formula

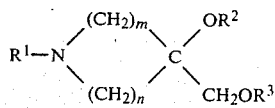

wherein R³, m and n have the starting values, R¹ is loweralkyl or phenyl-loweralkyl, and R² is loweralkyl or acyl.

Step 3—when required, debenzylating a compound prepared in Steps 1 or 2 wherein R¹ is benzyl to give a compound of the formula

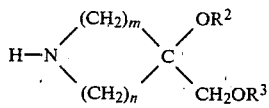

wherein R², R³, m and n are as defined in Step 3.

Step 4—when required, quaternerizing a compound prepared in Steps 1 or 2 by reacting with an R⁴X reagent wherein R⁴ is equivalent to R¹, except R¹ and R⁴ are never benzyl at the same time, and X is halo or sulfato to give a quaternary salt of the formula

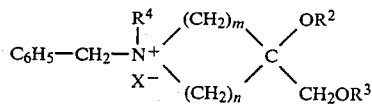

wherein R², R³, m, n, X and R⁴ have their starting values.

Step 5—when required, reacting the —NH compound prepared in Step 3 with a reagent R¹ halide and base in an aprotic solvent wherein R¹ is loweralkyl or phenyl-lower-alkyl other than benzyl to give a compound of the formula

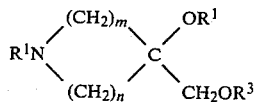

wherein R², R³, m and n have the same values as the product of Step 3 and R¹ is loweralkyl or phenyl-loweralkyl other than benzyl.

Step 6—alternatively reacting a halogen quaternary compound prepared in Step 4 wherein R¹ or R⁴ are benzyl with silver oxide (Ag₂O) and catalytically debenzylating, preferably with hydrogen, over palladium on carbon to give a compound of the formula

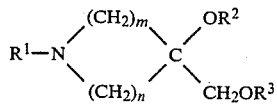

wherein R², R³, m and n have the same values as the product of Step 4 and R¹ is the same as in Formula I, except benzyl.

Step 7—alternatively reacting a compound prepared in Step 3 with formaldehyde, formic acid and water to obtain a compound of the formula

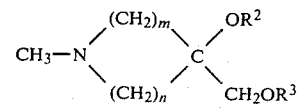

wherein R², R³, m and n have the same values as in Step 3.

Step 8—alternatively reacting a compound prepared in Step 3 wherein R² is hydrogen or loweralkyl and R¹ is hydrogen or benzyl with reagent R⁵—OC(O)Cl wherein R⁵ is loweralkyl or phenyl-loweralkyl followed by lithium aluminum hydride to give a compound of the formula

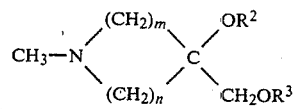

wherein R³, m and n have their starting values and R² is hydrogen or loweralkyl.

The following discussion is applicable to details of preparation of the active agents and related to the foregoing outlined process.

Preparation of the Aryloxymethyl Pyrrolidinols and Piperidinols

The reaction of the epoxide of Formula II in Step 1 wherein R¹ is other than hydrogen and an appropriately chosen phenol is carried out by mixing the reactants neat with a trace of an acidic catalyst, raising the temperature to 80°–150° C. until the reaction is complete or diluting the reactants with a non-polar non-protic solvent of the appropriate boiling point to ensure reaction. A work-up by standard methods permits isolation of the aryloxymethyl pyrrolidinols and piperidinols.

O-Alkylation and O-Acylation

O-Alkylation may be effected in Step 2 by reacting compounds of Formula I$_a$ (See Chart I; R¹ never H) with a loweralkyl halide, preferably in 10% excess and sodium hydride, preferably in slight excess in a solvent, preferably dimethylformamide. The reaction work-up and product isolation may be undertaken in a conventional manner. O-Acylation of the hydroxy radical of a Formula I$_a$ compound may be effected by reacting with a loweralkyl acid halide in an aprotic solvent together with a suitable base for absorbing the liberated acid, preferably alkali metal carbonate, and working up in a conventional manner or by reacting with a loweralkyl acid anhydride in pyridine solvent and working up in a conventional manner.

Debenzylation to Obtain Unsubstituted Pyrrolidinol and Piperidinol Derivative (R¹=H)

In Step 3, when the substituents in the aryl ring are not sensitive to reduction, catalytic debenzylation (under, e.g., Pd/C, H₂) is employed under standard reaction conditions by use of a Parr hydrogenation apparatus at 30–50 psi, 190–200 ethanol. When the substituents on the aryl ring are sensitive to catalytic hydrogenation, chemical debenzylation may be employed. Benzyl chloroformate or 2,2,2-trichloroethylchloroformate may be used. The reaction is typically carried out in a non-polar solvent such as benzene and the urethane group hydrolyzed or removed under acidic, basic or hydrogenation conditions or using zinc dust in an appropriate solvent (e.g., methanol or acetic acid as per the procedure described in Tet. Letters, 1967 (27), pp. 2555-7). Any of the benzyl compounds prepared in Steps 1 or 2 of the foregoing outlined process may be debenzylated.

Preparation of Quaternary Compounds

Any of the benzyl compounds prepared in Steps 1 or 2 may be converted to quaternary salts in conventional manner as illustrated in Examples 20 and 21 (See Step 4 of outlined process). The methyl iodide quaternary salt of the 1-benzyl derivatives is preferred.

N-Alkylation

N-Alkylation is conducted under standard conditions of the art using an $R^1$-halide and a base (see Step 5), preferably an alkali-metal carbonate. In Step 6, a halogen quaternary salt is reacted with silver oxide ($Ag_2O$) to give the hydroxide as an intermediate which is then subjected to catalytic debenzylation methods known in the art, e.g., preferably Pd/C+$H_2$). In Step 7, methylation may be effected by the Eschweiler-Clarke method (HCOOH—HCOH) starting with the —NH compound, i.e., a pyrrolidine or piperidine unsubstituted in the 1-position, under standard conditions. In Step 8, a compound wherein $R^2$ is H or lower-alkyl and $R^1$ is H or benzyl is reacted with reagent $R^5OCOCl$ followed by lithium aluminum hydride in solvent, preferably diethyl ether, to effect methylation. $R^5$ may be loweralkyl, phenyl or phenyl-loweralkyl. When $R^2$ is H, twice as much of the reagents are required.

Preparation of Free Bases

Free bases of the acid addition salts of compounds of Formula I may be regenerated by proportioning between an organic solvent such as methylene chloride and water or dilute aqueous basic solution and separating the solvent layer, drying and evaporating.

The following examples are provided merely by way of illustration and are not to be construed as being limiting in nature.

EXAMPLE 1

3-Phenoxymethyl-1-phenylmethyl-3-pyrrolidinol

A solution of 12.0 g (0.0634 mole) of 5-benzyl-1-oxa-5-azaspiro[2:4]heptane in 100 ml of anhydrous toluene was treated with 6.56 g (0.0697 mole) of phenol under a nitrogen atmosphere and the mixture refluxed for 18 hours. The mixture was cooled, and the solvent evaporated under reduced pressure. The residue (18.3 g) was dissolved in chloroform (150 ml), extracted with 3N sodium hydroxide (100 ml), water (100 ml), dried over magnesium sulfate and evaporated under reduced pressure (15.5 g). The residue was crystallized from cold isopropanol (freezer) to give 6.8 g of product, m.p., 80°-84° C. Two recrystallizations from cold isopropanol-water gave 4.5 g (25%) crystals, m.p. 82.5°-84° C. A sample was dried at room temperature and 0.10 mm Hg pressure for 24 hr.

Analysis: Calculated for $C_{18}H_{21}NO_2$: C,76.30; H,7.47; N,4.94 Found: C,75.93; H,7.50; N,4.85.

EXAMPLE 2

4-Phenoxymethyl-1-phenylmethyl-4-piperidinol Hydrobromide [1:1]

A solution of 47.5 g (0.2337 mole) of 6-benzyl-1-oxa-6-azaspiro[2:5]octane, 26.3 g (0.2804 mole) of phenyl, two drops of water and 0.1 g of toluene-sulfonic acid monohydrate in 400 ml of anhydrous toluene was refluxed under a nitrogen atmosphere for 26 hours. The solvent was evaporated under reduced pressure and NMR analysis of the residue indicated that very little reaction had occurred. The residue was warmed to 120° C. under a nitrogen atmosphere and stirred at this temperature overnight (16 hr). The mixture was cooled to room temperature, dissolved in chloroform (250 ml), extracted with 3N sodium hydroxide (2×125 ml), water (125 ml), dried over magnesium sulfate and evaporated under reduced pressure (59.3 g). The residue was dissolved in anhydrous ether (500 ml) and treated with hydrogen bromide gas until no further precipitation occurred. The solid was triturated well, filtered, washed well with ether and dried. The crude salt was recrystallized from isopropanol: 37.2 g (42%), m.p. 180°-183° C. Recrystallization of a 15.0 g sample from isopropanol gave 11.9 g crystals, m.p. 182°-185° C. which was dried at 56° C. and 0.01 mm Hg pressure overnight.

Analysis: Calculated for $C_{19}H_{24}BrNO_2$: C,60.32; H,6.39; N,3.70: Found: C,60.12; H,6.42; N,3.65.

EXAMPLE 3

3-[(2-Ethoxyphenoxy)methyl]-1-phenylmethyl-3-pyrrolidinol

A stirred mixture of 56.1 g (0.294 mole) of 5-benzyl-1-oxa-5-azaspiro[2:4]heptane and 49.2 g (0.3557 mole) of 2-ethoxyphenol was heated at 100°±2° C. under a nitrogen atmosphere for 2.5 hours. The reaction mixture was cooled to room temperature, dissolved in chloroform (250 ml), extracted with 3N sodium hydroxide (2×125 ml), and the combined basic extracts extracted with chloroform (125 ml). The combined chloroform solutions were extracted with water (250 ml), dried over magnesium sulfate, and evaporated under reduced pressure (94.0 g). The residue was dissolved in benzene and chromatographed on a 1.5 kg column of Florisil packed in benzene. Product was eluted with increasing concentrations of methanol in benzene (1 to 9%). Crystalline solid, 84.6 g was obtained which was recrystallized from isooctane to give 66.0 g crystals (68%), m.p. 56.5°-59° C. A portion of the recrystallized product was dried at room temperature and 0.01 mm Hg for 4 hours.

Analysis: Calculated for $C_{20}H_{25}NO_3$: C,73.37; H,7.70; N,4.28; Found: C,73.47; H,7.70; N,4.25.

EXAMPLE 4

4-Phenoxymethyl-4-piperidinol Hydrochloride [1:1]

A solution of 14.3 g (0.0481 mole) of 1-benzyl-4-phenoxymethyl-4-piperidinol and 8.37 g (0.106 mole) of pyridine in 150 ml of anhydrous benzene was treated dropwise under a nitrogen atmosphere with a solution of 19.04 g (0.106 mole) of benzylchloroformate in 50 ml of anhydrous benzene. After stirring overnight at room temperature, water (200 ml) was added, the layers separated, the benzene layer dried over magnesium sulfate and evaporated under reduced pressure. NMR analysis indicated that reaction had occurred exclusively at the 4-hydroxy position. The residue was dissolved in 150 ml of anhydrous benzene, treated dropwise with a solution of 10.36 g (0.05772 mole) of benzylchloroformate in 50 ml of anhydrous benzene and stirred overnight at room temperature. The solvent was removed under reduced pressure, and the residue washed well with pet. ether (30°-60° C.) to remove benzylchloride, NMR analysis indicated approximately 50% reaction. The residue was dissolved in chloroform, extracted with saturated aqueous sodium bicarbonate (75 ml), water (75 ml), and evaporated under reduced pressure (13.7 g). The residue was dissolved in 200 ml of absolute ethanol and shaken overnight while being heated under a hydrogen atmosphere using palladium-on-carbon as catalyst. The catalyst was removed by filtration and the filtrate evaporated under reduced pressure (9.7 g). NMR analysis showed that the benzyloxyformate group had been removed, but not the N-benzyl. Additional 1-benzyl-4-phenoxy-methyl-4-piperidinol (2.8 g) was added, the whole dissolved in 175 ml of absolute ethanol, and an equivalent of 1N hydrochloric acid (43 ml, 0.043 mole) was added. The reaction mixture was pulled briefly under reduced pressure to remove any excess hydrochloric acid, treated with Pd/C catalyst, warmed, and shaken overnight under a hydrogen atmosphere. Analysis by TLC (20% methanol benzene) showed partial reaction, so the reaction vessel was returned to the Parr hydrogenator and heated and shaken under a hydrogen atmosphere over the weekend (2.5 days). The catalyst was removed by filtration and the filtrate evaporated under reduced pressure, (15.5 g of white solid). Recrystallization from isopropanol gave 5.7 g of the hydrochloride salt (48.7%), m.p. 203°–205° C. A sample was dried at 79° C. and 0.01 mm Hg pressure for 6 hours.

Analysis: Calculated for $C_{12}H_{18}ClNO_2$: C,59.14; H,7.44; N,5.57: Found: C,59.00; H,7.48; N,5.90.

EXAMPLE 5

3-[(2-Ethoxyphenoxy)methyl]-3-pyrrolidinol

A solution of 10.0 g (0.0305 mole) of 1-benzyl-3-(2-ethoxyphenoxy)methyl-3-pyrrolidinol in 125 ml of absolute ethanol was treated with Pd/C catalyst and warmed while shaking under a hydrogen atmosphere on a Parr hydrogenation apparatus for 16 hours. The catalyst was removed by filtration and the filtrate evaporated under reduced pressure. The white crystalline residue (7.1 g) was recrystallized from benzene isooctane to yield 6.6 g of product (91%), m.p. 108°–110° C.

Analysis: Calculated for $C_{13}H_{19}NO_3$: C,65.80; H,8.07; N,5.90; Found: C,65.71; H,8.00; N,5.81.

EXAMPLE 6

3-[(2-Ethoxyphenoxy)methyl]-3-methoxy-1-phenylmethylpyrrolidine Oxalate [1:1]

Sodium hydride (2.83 g, 0.0672 mole, 57% mineral oil suspension) was washed three times with pet. ether (30°–60°), suspended in 60 ml of freshly distilled anhydrous dimethylformamide and treated slowly with a solution of 20.0 g (0.0611 mole) of 1-benzyl-3-(2-ethoxyphenoxy)methyl-3-pyrrolidinol in 60 ml of anhydrous dimethylformamide. The reaction mixture was warmed to approximately 80° C. and stirred for 0.25 hours until evolution of hydrogen ceased. The mixture was cooled to room temperature and treated slowly with a solution of 9.54 g (0.00672 mole) of methyl iodide in 50 ml of anhydrous dimethylformamide. The mixture was stirred overnight at room temperature under a nitrogen atmosphere. The reaction mixture was cautiously diluted with water (200 ml) and extracted with ether (3×200 ml). The combined ether extracts were extracted with water (250 ml), dried over magnesium sulfate and evaporated under reduced pressure (20.5 g). The residue was combined with that from a trial reaction (3.0 g), dissolved in benzene and chromatographed on a 500 g column of florisil packed in benzene. Elution with benzene, then 1–2% methanol/benzene gave 20.0 g of pure compound (95.8%). A 5.6 g sample (0.0164 mole) of the compound was dissolved in hot isopropanol and treated with a solution of 2.07 g (0.0164 mole) of oxalic acid dihydrate in hot isopropanol. Upon cooling, a solid precipitated. Three crops of material were obtained (5.6, 0.6, and 0.4 g). The first two were amorphous, the last crystalline with a m.p. of 89°–91° C. The three were combined and recrystallized from isopropanol to give 5.4 g crystals, m.p. 101°–104° C. The material was dried at 62° C. and 0.01 mm Hg pressure for 6 hours, then at room temperature and 0.1 mm Hg pressure for 16 hours.

Analysis: Calculated for $C_{23}H_{29}NO_7$: C,64.02; H,6.77; N,3.25; Found: C,64.07; H,6.86; N,3.28.

EXAMPLE 7

3-[(2-Ethoxyphenoxy)methyl]-3-methoxypyrrolidine Fumarate [1:1]

A solution of 13.3 g (0.03895 mole) of 3-[(2-ethoxyphenoxy)methyl]-3-methoxy-1-phenylmethylpyrrolidine in 150 ml of absolute ethanol was treated with Pd/C catalyst and shaken under a hydrogen atmosphere while heating at approximately 60°–70° C. for 16 hours. TLC analysis showed that the reaction was not complete. Additional catalyst was added and the reaction mixture was subjected to the same conditions for 6 hours. After standing at room temperature over the weekend, the catalyst was removed by filtration and the filtrate evaporated under reduced pressure (8.9 g). A solution of 7.7 g (0.0308 mole) of the product in hot isopropanol was treated with a solution of 3.57 g (0.0308 mole) of fumaric acid in hot isopropanol and then treated with isopropyl ether. On filtration there was obtained 7.2 g of fumarate salt, m.p. 92°–97° C. Recrystallization from ethanol-isopropyl ether gave 4.5 g (31.5%) crystals, m.p. 103°–107° C. Drying overnight at 62° C. and 0.10 mm Hg pressure raised the m.p. to 107°–109° C.

Analysis: Calculated for $C_{18}H_{25}NO_7$: C,58.85; H,6.86; N,3.81; Found: C,58.76; H,6.87; N,3.89.

EXAMPLE 8

3-[(1-Naphthalenyloxy)methyl]-1-phenylmethyl-3-pyrrolidinol

A mixture of 18.9 g (0.1 mole) of 5-benzyl-1-oxa-5-azaspiro[2.4]heptane and 15.6 g (0.11 mole) of 1-naphthol was heated to 115° C. to form a homogenous melt, which was stirred with a magnetic stirrer for 2 hours. Upon cooling, a paste-like material formed. The reaction mixture was dissolved in benzene, filtered and ligroin added to the filtrate until cloudy. The suspension was warmed to solution and allowed to stand in the refrigerator overnight. The precipitate was collected by filtration to give 20.2 g (60%) of crude material. A portion of this solid was recrystallized from 190 ethanol to give a white crystalline solid, m.p. 129.5°–130° C.

Analysis: Calculated for $C_{22}H_{23}NO_2$: C,79.25; H,6.95; N,4.20; Found: C,79.01; H,6.93; N,4.19.

EXAMPLE 9

3-[(1-Naphthalenyloxy)methyl]-3-pyrrolidinol Hydrochloride [1:1]

A slurry of 12 g (0.036 mole) of 3-(1-naphthalenyloxy)methyl-1-phenylmethyl-3-pyrrolidinol in 200 ml of 200 ethanol was treated with 0.5 g of 10% Pd/C catalyst and shaken under 50 psi of $H_2$ pressure in a Parr apparatus at 80° C. for 20 hr. Hydrogen uptake was approximately 6 lb. The Parr bomb was cooled and the catalyst removed by filtration under a nitrogen atmosphere. The filtrate was concentrated using a rotary evaporator to give a paste. Trituration with 30°-60° C. pet. ether gave a solid which was separated and recrystallized from benzene-ligroin. The solid was converted to the hydrochloride salt using ethereal hydrogen chloride and crystallized from isopropyl alcohol-ethyl ether to give 9.5 g of the salt (95%), m.p. 200°-201° C.

Analysis: Calculated for $C_{15}H_{18}NO_2Cl$: C,64.40; H,6.49; N,5.01; Found: C,64.16; H,6.47; N,5.05.

EXAMPLE 10

3-[[(1H-2,3-Dihydroinden-4-yl)oxy]methyl]-1-phenylmethyl-3-pyrrolidinol

5-Benzyl-1-oxa-5-azaspiro[2.4]-heptane (18.9 g; 0.1 mole) was heated to 110° C. under nitrogen and while stirring, 15.06 g (0.11 mole) of 4-indanol was added in a single portion. The temperature increased to 135° C. and the reaction mixture was stirred without further heat for 45 min during which the temperature had dropped to 75° C. The crude reaction product was chromatographed on a 300 g column of florisil and eluted with benzene (six fractions collected with poor separation). The column was then eluted with an acetone-benzene gradient. The residue from the ninth fraction solidified when triturated with 30°-60° C. pet. ether. All the fractions were combined and crystallized from 30°-60° C. pet. ether to yield 17 g of off-white powder (52.6%), m.p. 80°-81° C.

Analysis: Calculated for $C_{21}H_{25}NO_2$: C,77.99; H,7.79; N,4.33; Found: C,78.64; H,7.81; N,4.34.

EXAMPLE 11

3-[[(1H-2,3-Dihydroinden-4-yl)oxy]methyl]-3-pyrrolidinol Hydrochloride [1:1]

A solution of 11 g (0.034 mole) of 3-[[(1H-2,3-dihydroinden-4-yl)oxy]methyl]-1-phenylmethyl-3-pyrrolidinol in 150 ml of 190 ethanol was treated with 10% Pd/C catalyst and shaken overnight at 70° C. under 40 psi of hydrogen in a Parr apparatus. The catalyst was removed by filtration and the filtrate concentrated to a pale yellow oil. The residual oil was dissolved in isopropyl alcohol and saturated with hydrogen chloride gas. Upon addition of ethyl ether, a gummy substance separated then solidified. Recrystallization from isopropyl alcohol-isopropyl ether gave 6.6 g of the off-white crystalline salt (72%), m.p. 149.5°-151° C.

Analysis: Calculated for $C_{14}H_{20}ClNO_2$: C,62.33; H,7.47; N,5.19; Found: C,62.31; H,7.42; N,5.36.

EXAMPLE 12

3-Ethoxy-3-[(2-ethoxyphenoxy)methyl]pyrrolidine Hydrochloride [1:1]

A solution of 10.4 g (0.029 mole) of 1-benzyl-3-ethoxy-3-[(2-ethoxyphenoxy)methyl]pyrrolidine in 100 ml of 200 ethanol was treated with palladium/carbon catalyst and shaken at 70° C. under a hydrogen atmosphere for 16 hours. No hydrogen was absorbed. The catalyst was removed by filtration, the filter cake washed with 50 ml of 200 ethanol, the filtrate transferred to a Parr reaction bottle and treated with 29 ml of 1.00N hydrochloric acid. Palladium/carbon catalyst was added and the reaction mixture was shaken under a hydrogen atmosphere at 70° C. for 16 hours. The catalyst was removed by filtration, and the filtrate evaporated under reduced pressure (9.0 g). The product hydrochloride crystallized on standing and was recrystallized twice from isopropanol-isopropyl ether: 5.7 g, (65%), m.p., 109°-112° C. The salt was dried under vacuum.

Analysis: Calculated for $C_{15}H_{24}ClNO_3$: C,59.69; H,8.12; N,4.64; Found: C,59.75; H,7.89; N,4.84.

EXAMPLE 13

3-Ethoxy-3-[(2-ethoxyphenoxy)methyl]-1-phenylmethylpyrrolidine Oxalate [1:1]

Sodium hydride, 3.44 g (0.0816 mole) in 57% mineral oil suspension was washed three times with petroleum ether (30°-60° C.) under nitrogen atmosphere, suspended in 60 ml of freshly distilled anhydrous dimethylformamide and treated slowly with a solution of 24.3 g (0.0742 mole) of 1-benzyl-3-(2-ethoxyphenoxy)methyl-3-pyrrolidinol in 60 ml of freshly distilled anhydrous dimethylformamide. After hydrogen evolution had ceased, a solution of 11.6 g (0.0742 mole) of ethyl iodide in 60 ml of freshly distilled anhydrous dimethylformamide was added dropwise under a nitrogen atmosphere. The reaction mixture was stirred at room temperature for 16 hours (overnight), then cautiously diluted with 50 ml of water and poured into 1500 ml of water. The suspension was extracted with chloroform ($3 \times 200$ ml) and the combined chloroform extracts washed with water ($3 \times 200$ ml), dried over magnesium sulfate and evaporated under reduced pressure (26.1 g). The crude product which contained starting material was dissolved in benzene and chromatographed on a 500 g column of florisil packed in benzene. The column was eluted with benzene and methanol-benzene solvent mixtures. The fractions containing product were combined and evaporated under reduced pressure. Weight of residue was 15.0 g (57%). A mixture of 3.0 g (0.0084 mole) of the product and 1.06 g (0.0084 mole) of oxalic acid dihydrate in isopropanol was warmed to solution, filtered, and the filtrate seeded. The oxalate salt, 3.4 g, was collected by filtration, m.p. 125°-127° C. The material was recrystallized twice from isopropanol-isopropyl ether leaving 0.8 g of salt, m.p. 127°-129° C., which did not analyze as expected. The filtrate gave a second crop, 1.0 g, m.p. 125°-127° C. which was dried at 62° C. and 0.01 mm pressure for 4 hours and at room temperature and 0.01 mm pressure overnight.

Analysis: Calculated for $C_{24}H_{31}NO_7$: C,64.70; H,7.01; N,3.14; Found: C,64.24; H,7.08; N,3.51.

EXAMPLE 14

4-[(1-Naphthalenyl)oxy]methyl]-4-piperidinol Hydrochloride [1:1]

A solution of 14 g (0.04 mole) of 1-benzyl-4-[[(1-naphthalenyl)oxy]methyl]-4-piperidinol in 150 ml of 200 ethanol was treated with 10% Pd/C catalyst and shaken overnight at 78° C. under 40 psi of hydrogen in a Parr apparatus. The catalyst was removed by filtration and the filtrate concentrated under reduced pressure to a pale amber oil (9.2 g). A solution of the residual oil in isopropyl alcohol was treated with ethereal hydrogen chloride and isopropyl ether added to induce crystallization. Filtration afforded 8.5 g of the hydrochloride salt as white crystals (76%), m.p. 243° C. (decomposition).

Analysis: Calculated for $C_{16}H_{20}ClNO_2$: C,65.41; H6.86; N,4.77; Found: C65.50; H,6.76; N,4.77.

EXAMPLE 15

4-[(1-Naphthalenyloxy)methyl]-1-phenylmethyl-4-piperidinol Hydrochloride [1:1]

A mixture of 26.5 g (0.13 mole) of 6-benzyl-1-oxa-6-azaspiro[2.5]octane and 2.08 g (0.0145 mole) of 1-naphthol was heated to 100° C. The melt which formed was stirred with a magnetic stirrer while an additional 20.84 g (0.145 mole) of 1-naphthol was added in 2 g portions. The reaction became exotheric and the temperature increased to 110° C. After stirring for 1 hr, TLC analysis (10% methanol/benzene) showed one major spot. The reaction mixture was cooled to 60° C., dissolved in benzene, washed with 3N sodium hydroxide (3×50 ml), and dried over magnesium sulfate. The drying agent was removed by filtration and the solvent removed under reduced pressure to give 49.2 g of green oil. The oil was chromatographed on a 1.5 kg column of florisil (60-100 mesh) and eluted with a benzene-acetone gradient. A total of 6 major fractions were collected. Of these, fractions 3 and 4 gave 21 g of nearly pure product (46.6%). Fraction 4 (7 g) was dissolved in isopropyl ether and treated with ethereal hydrogen chloride to give an oil which solidified when triturated with fresh isopropyl ether. The solid was recrystallized 3 times from isopropanol-isopropyl ether after treating with charcoal to give 3.3 g of crystalline product as the hydrochloride salt, m.p. 166°-169° C. After drying at 80° C. at reduced pressure, the melting point increased to 170°-171.5° C.

Analysis: Calculated for $C_{23}H_{26}N_1O_2Cl_1$: C,71.96; H,6.83; N,3.65; Found: C,71.66; H,6.83; N,3.42.

EXAMPLE 16

4-[[(1H-2,3-Dihydroinden-4-yl)oxy]methyl]-1-phenylmethyl-4-piperidinol Hydrochloride [1:1]

A sample of 20.5 g (0.1 mole) of 6-benzyl-1-oxa-6-azaspiro[5.2]octane was heated to 100° and treated portionwise while stirring with 13.5 g (0.1 mole) of 4-indanol. After stirring for 45 min, the reaction was shown by TLC analysis to be approximately 50% complete. Stirring was continued for 1 hr, but TLC analysis showed no change in product formation. An additional 7.0 g (0.05 mole) of 4-indanol was added, and the reaction mixture stirred for 1 hr at 100° C. at which time TLC analysis showed the reaction to be 80-90% complete. The reaction mixture was cooled, diluted with benzene, and extracted with six 200 ml portions of 3N hydrochloric acid. The acidic extracts were combined and the pH was adjusted to neutral using 3N sodium hydroxide. The aqueous suspension was extracted with benzene and the combined extracts dried over magnesium sulfate and evaporated under reduced pressure to a dark oil. The residual oil was dissolved in acetonitrile and while stirring, treated with an equivalent of oxalic acid (0.1 mole) dissolved in 100 ml of methanol. The solid which separated was collected by filtration to give 37.5 g of wet product, m.p. 181°-191° C. Recrystallization from methanol left 22.2 g of the oxalate salt as beige crystals, m.p. 200°-201° C. with degassing. The oxalate salt was converted to the free base by partitioning between dilute aqueous base and methylene chloride and evaporating the methylene chloride layer to give a residual oil (14 g). A solution of approximately 7 g of the residual oil in acetonitrile was treated with ethereal hydrogen chloride to give 6.8 g of the hydrochloride salt in two crops, m.p. 125°-129° C. and 127°-130° C. The two solids were combined and recrystallized from isopropanol-isopropyl ether (after charcoal treatment) to give 5.3 g of the hydrochloride salt as fine white crystals, m.p. 189°-190° C.

Analysis: Calculated for $C_{22}H_{28}N_1O_2Cl_1$: C,70.67; H,7.55; Found: C,70.56; H,7.59; N,3.66.

EXAMPLE 17

4-[[(1H-2,3-Dihydroinden-4-yl)oxy]methyl]-4-piperidinol Hydrochloride

A solution of 7 g (0.02 mole) of 4-[[(1H-2,3-dihydroinden-4-yl)oxy]methyl]-1-phenylmethyl-4-piperidinol in 75 ml of 200 ethanol was treated with 10% Pd/C catalyst and shaken overnight at 75° C. in a Parr hydrogenation apparatus. The catalyst was removed by filtration and the filtrate was treated with ethereal hydrogen chloride, then concentrated under reduced pressure. The residue was dissolved in hot isopropanol and the volume reduced until crystallization began. After cooling, the precipitate was collected by filtration to give 4.8 g of the hydrochloride salt (84.6%), m.p. 217°-218° C. dec.

Analysis: Calculated for $C_{15}H_{22}N_1O_2Cl$: C,63.48; H,7.87; N,4.94; Found: C,63.33; H,7.91; N,4.93.

EXAMPLE 18

4-[(2-Ethoxyphenoxy)methyl]-1-phenylmethyl-4-piperidinol Compound with N-cyclohexylsulfamic acid [1:1]

A mixture of 41.0 g (0.2 mole) of 6-benzyl-1-oxa-6-azaspiro[2.5]octane and 41.4 g (0.3 mole) of 2-ethoxyphenol was treated with 1 drop of conc. sulfuric acid and heated on a steam bath to form a homogenous melt. The reaction was followed by TLC and was complete after heating on the steam bath for 96 hr. The reaction mixture was cooled, dissolved in 300 ml of chloroform, washed with 4-200 ml portions of 3N sodium hydroxide, then 2-100 ml portions of water. The chloroform solution was extracted with 3-300 ml portions of 10% hydrochloric acid, but the hydrochloride salt was insoluble in water and remained in the organic phase. The chloroform solution was shaken with 3N sodium hydroxide, extracted with water, dried over magnesium sulfate, filtered and evaporated under a reduced pressure to give 62 g of an amber oil. The residual oil was dissolved in isopropyl ether and filtered through celite to remove a small amount of colloidal precipitate. The filtrate was treated with oxalic acid in isopropanol in the usual manner to give the oxalate salt 67.2 g, m.p. 102°-104° C. A small sample was recrystallized from acetone-isopropyl ether to give a m.p. of 103°-104° C. Analysis (NMR) suggested that the salt was the half isopropyl ester of the oxalic acid salt, rather than the oxalic acid salt. Elemental analyses were in agreement with this structure. The bulk sample of the oxalate salt was converted to 38 g of the free base as in Example 16. A 6 g sample was converted to the hexamic acid (cyclohexylsulfamic acid) salt by reacting with cyclohexylsulfamic acid in isopropyl alcohol and recrystallized from isopropanol-isopropyl ether to give 6.5 g of pale yellow crystals, m.p. 121°-122° C.

Analysis: Calculated for $C_{27}H_{40}N_2O_6S_1$: C,62.28; H,7.74; N,5.38; Found: C,62.36; H,7.81; N,5.31.

EXAMPLE 19

4-[(2-Ethoxyphenoxy)methyl]-4-piperidinol Hydrochloride [1:1]

A solution of 6.5 g (0.02 mole) of 4-[(2-ethoxyphenoxy)methyl]-1-phenylmethyl-4-piperidinol in 100 ml of 200 ethanol was treated with 0.5 g of 10% Pd/C catalyst and shaken under 42 psi of hydrogen for 20 hr at 70° C. in a Parr apparatus. The catalyst was removed by filtration and the filtrate treated with ethereal hydrogen chloride. Gummy precipitate solidified on trituration with ethyl ether and was recrystallized from isopropanol-isopropyl ether to give 5.5 g (96%) of the hydrochloride salt as off-white, fine needles, m.p. 148°-149° C.

Analysis: Calculated for $C_{14}H_{22}N_1O_3Cl_1$: C,58.43; H,7.71; N,4.87; Found: C,58.28; H,7.82; N,4.72.

EXAMPLE 20

4-[(2-Ethoxyphenoxy)methyl]-4-hydroxy-1-methyl-1-phenylmethylpiperidinium Iodide A solution of 6.5 g (0.02 mole) of 4-[(2-ethoxyphenoxy)methyl]-1-phenylmethyl-4-piperidinol in 100 ml of dry acetone was stirred at 10° C. while 4.2 g (0.03 mole) of methyl iodide was added in one portion. The solution was warmed to 30° C. and allowed to cool while stirring overnight. The solid precipitate was collected by filtration to yield 7 g (72.5%) of pale yellow crystals, m.p. 187°-189° C.

Analysis: Calculated for $C_{22}H_{30}N_1O_3I_1$: C,54.69; H,6.26; N,2.90; Found: C,54.45; H,6.30; N,2.78.

EXAMPLE 21

4-[(2-Ethoxyphenoxy)methyl]-4-methoxy-1-methyl-1-phenylmethylpiperidinium Iodide A mixture of 2 g (0.05 mole) of 50% sodium hydride and 50 ml of dry dimethylformamide was stirred at 60° C. under a nitrogen atmosphere while a solution of 14.2 g (0.042 mole) of 4-[(2-ethoxyphenoxy)methyl]-1-phenylmethyl-4-piperidinol in 50 ml of dry dimethylformamide was added dropwise at such a rate to maintain steady evolution of hydrogen. When the evolution of hydrogen ceased the reaction mixture was stirred at 60° C. for 5 hr. The deep amber solution was cooled to 10° C. and 5.9 g (0.05 mole) of methyl iodide was added in one portion. After stirring at room temperature for 62 hr, the reaction solution was poured into ice water and extracted with 3-100 ml portions of benzene. The extracts were combined and washed with 100 ml of water, 100 ml of 6N hydrochloric acid, and with 50 ml of water. The first wash was discarded. The acid portion and last water wash were combined, made basic with 3N sodium hydroxide and extracted into benzene. The benzene was dried over magnesium sulfate, filtered and concentrated in vacuo to give 8.3 g of dark oil, identified by NMR spectroscopy as a 80%-20% mixture of the expected product, 4-[(2-ethoxyphenoxy)methyl]-4-methoxy-1-phenylmethyl-piperidine and starting material. A precipitate formed in the original dimethylformamide/water portion of the work-up and it was collected by filtration to give 9.5 g solid. Mass and NMR spectra identified this material as the quarternary iodide salt of the expected product. The solid was triturated in hot acetone and filtered to give 5.1 g of pale yellow crystals, m.p. 185°-190° C. (decomposition).

Analysis: Calculated for $C_{23}H_{32}N_1O_3I_1$: C,55.54; H,6.48; N,2.82; Found: C,55.48; H,6.51; N,2.80.

EXAMPLE 22

4-[(2-Ethoxyphenoxy)methyl]-1-methyl-4-piperidinol Sesquifumarate

A solution of 6.7 g (0.0187 mole) of 4-[2-ethoxyphenoxy)methyl]-4-piperidinol in 6 ml of 88% formic acid was treated with 2.8 g of paraformaldehyde and heated on a steam bath until the evolution of carbon dioxide ceased, approximately 45 min. The reaction mixture was diluted with water, washed with a single 20 ml portion of benzene and made basic with 3N sodium hydroxide. The basic solution was extracted with 2-30 ml portions of benzene and these extracts were combined, dried over magnesium sulfate, filtered and concentrated in vacuo to a brown oil, 4 g. The oil was converted to the fumarate salt and recrystallized from acetone to give a white crystalline product, 3.8 g, m.p. 144°-146° C. Recrystallization from acetone then isopropanol-isopropyl ether left 1.8 g, m.p. 144°-145° C. The compound was shown by NMR spectroscopy to be the sesquifumarate salt, which was confirmed by elemental analyses.

Analysis: Calcuted for $C_{21}H_{29}N_1O_9$: C,57.40; H,6.65; N,3.19; Found: C,57.09; H,6.64; N,3.08.

EXAMPLE 23

3-[(2-Ethoxyphenoxy)methyl]-1-phenylmethyl-3-pyrrolidinol acetate ester oxalate [1:1]

A solution of 1.0 g (0.003 mole) of 3-[(2-ethoxyphenoxy)methyl]-1-phenylmethyl-3-pyrrolidinol in 10 ml of pyridine was treated with 1.0 ml of acetic anhydride and stirred for several days. The solvent was removed under reduced pressure and the residue partitioned between 10 ml of water and 10 ml of chloroform. The mixture was stirred for 3.0 hours, the organic layer separated, dried over magnesium sulfate and evaporated under reduced pressure (1.1 g). A mixture of the residue and 0.37 g (0.00298 mole) of oxalic acid dihydrate in isopropanol was warmed to solution, filtered, treated with isopropyl ether and allowed to cool slowly to room temperature. The oxalate salt was collected by filtration (1.0 g, m.p. 94°-96° C.) and recrystallized from isopropanol-isopropyl ether: 0.7 g (64%), m.p. 94.5°-96° C. The salt was dried overnight at 62°/0.10 mm Hg pressure.

Analysis: Calculated for $C_{24}H_{29}NO_8$: C,62.74; H,6.36; N,3.05; Found: C,62.45; H,6.43; N,2.98.

EXAMPLE 24

4-[(4-Chlorophenoxy)methyl]-1-phenylmethyl-4-piperidinol

A solution of 3.8g (0.03 mole) of 4-chlorophenol in 20 ml of dry dimethylformamide was stirred under a nitrogen atmosphere while 1.98 g of 85% potassium hydroxide was added. The resulting mixture was heated at 90° while stirring until all the potassium hydroxide dissolved. A solution of 4 g (0.02 mole) of 6-phenyl-1-oxa-6-azaspiro [5.2]octane in 10 ml of dimethylformamide was slowly added without further heating and the reaction mixture stirred at room temperature for 20 hr. The reaction mixture was poured into ice water. A crystalline mass separated and was collected by filtration to give 9 g of wet product. Recrystallization from benzene-ligroin gave 4.5 g of product as white plates (68%), m.p. 103°–103.5° C. The material was dried at 78° C. and 0.1 mm Hg pressure overnight. The melting point did not change.

Analysis: Calculated for $C_{19}H_{22}N_1O_2Cl_1$: C,68.77; H,6.69; N,4.22; Found: C,68.89; H,6.72; N,4.15.

EXAMPLE 25

4-[(4-Chlorophenoxy)methyl]-4-piperidinol

A solution of 20 g (0.06 mole) of 1-benzyl-4-[(4-chlorophenoxy)methyl]-4-piperidinol in 200 ml of pyridine/benzene (50/50) was stirred under nitrogen while 25.4 g (0.12 mole) of 2,2,2-trichloroethylchloroformate in 50 ml of benzene was added dropwise. The reaction mixture was stirred for 18 hours then diluted with 250 ml of water. The benzene layer was separated and the aqueous layer extracted with 2×50 ml of benzene. The benzene fractions were combined, dried over magnesium sulfate and concentrated in vacuo to give a dark oil; 23 g. The residual oil (ca. 0.039 mole) was dissolved in 250 ml of methanol and treated with 23 g of zinc dust. The mixture was heated at reflux for 24 hours while stirring under nitrogen. The reaction mixture was poured into an ice water slurry. A precipitate formed which was removed by filtration. The filtrate was extracted with three 50 ml portions of benzene then with two 100 ml portions of chloroform. None of these extracts contained any product. The aqueous methanol solution was evaporated under reduced pressure to give 15 g of yellow-green oil. Trituration of this residual oil with isopropyl ether gave 7.7 g of solid, m.p. 121°–124° C. identified as the expected product by NMR spectroscopy. Trituration of the filtrate residue gave a second crop of product (3 g). The solids were combined and recrystallized from acetone-isopropyl ether (1:10) to give 7.8 g of product, m.p. 124.5°–0.25° C.

Analysis: Calculated for $C_{12}H_{16}NO_2Cl$: C,59.63; H,6.67; N,5.80; Found: C,59.50; H,6.69; N,5.66.

EXAMPLE 26

4-[(2,6-Dichlorophenoxy)methyl]-1-phenylmethyl-4-piperidinol Hydrochloride.[1:1]

The potassium salt of 2,6-dichlorophenol was formed by heating at 76° C. a mixture of 6.6 g (0.1 mole) of potassium hydroxide pellets (85%) and 16.3 (0.1 mole) of 2,6-dichlorophenol in 150 ml of dry dimethylformamide until a clear brown solution was obtained. The stirred solution was treated dropwise with 20.3 g (0.1 mole) of 6-benzyl-1-oxa-6-azaspiro[2.5]octane in 50 ml of dry dimethylformamide and heated at 80° C. for 120 hours. TLC (5% methyl benzene/silica gel G) indicated that the reaction was only 40% complete. The reaction mixture was treated with 4 volumes of water and the suspension extracted with three 100 ml portions of benzene. The extracts were combined, washed with 50 ml of 3N sodium hydroxide followed by three 50 ml portions of water, dried over magnesium sulfate and evaporated under reduced pressure to give 26.2 g of dark brown oil. The oil was chromatographed on a 500 g column of silica gel 60 and eluted with benzene followed by 1 to 10% acetone-benzene gradient. A small amount of 2,6-dichlorophenol was collected and discarded. The column was then eluted with a mixture of 1% methanol and 10% acetone in benzene. Fractions containing the product were combined and evaporated under reduced pressure to give 10.5 g of a yellow oil. The residual oil was converted to the hydrochloride salt in the usual way and recrystallized from acetone to give 5.2 g of product, m.p. 203°–205° C. with a phase change at 140°–153° C.

Analysis: Calculated for $C_{19}H_{22}NO_2Cl_3$: C,56.66; H,5.51; N,3.48; Found: C,56.57; H,5.42; N,3.42.

EXAMPLE 27

1-Methyl-3-(phenoxymethyl)-3-piperidinol Hydrochloride [1:1]

A solution of 5 g (0.024 mole) of crude 3-(phenoxymethyl)-3-piperidinol monohydrochloride and 5 g (0.096 mole) of formic acid (88%) in 10 ml of water was treated with 3 ml (0.036 mole) of formalin (37%) and heated on a steam bath for 18 hours. The reaction mixture was diluted with water, made basic with 3N sodium hydroxide, and extracted with three 40 ml portions of methylene chloride. The extracts were combined over magnesium sulfate, filtered, and evaporated under reduced pressure to give a pale yellow oil (4.2 g). The oil was chromatographed on a 400 g column of florisol using an acetone-benzene gradient (0–2%) to elute the product. Fractions containing nearly pure product were combined and evaporated under reduced pressure. The residual oil was dissolved in acetone, treated with ethereal hydrogen chloride and allowed to stand overnight. Filtration afforded 1.8 g solid, which was recrystallized from cold acetone (charcoal pretreatment) to give 1.3 g of hydrochloride salt, m.p. 151°–152° C.

Analysis: Calculated for $C_{13}H_{20}NO_2Cl$: C,60.58; H,7.82; N,5.43; Found: C,60.58; H,7.84; N,5.47.

EXAMPLE 28

3-(Phenoxymethyl)-1-(phenylmethyl)-3-piperidinol Hydrochloride [1:1]

A mixture of 6.95 g (0.074 mole) of phenol, 15 g (0.074 mole) of 5-benzyl-1-oxa-5-azaspiro[2.5]octane, 4.19 g (0.063 mole) of potassium hydroxide (85%), and 100 mg of 18-crown-6-ether in 200 ml of toluene was heated at reflux for 4 hours and stirred overnight without further heating. The reaction mixture was diluted with 200 ml of benzene and washed with three 100 ml portions of water. The organic solution was filtered to remove a fine amorphous solid and the filtrate extracted with 20 ml of 6N hydrochloric acid. The acid layer was separated and the organic layer extracted with 25 ml of water. The aqueous and acid extracts were combined and evaporated under reduced pressure to give a dark viscous oil (17.8 g). The hydrochloride salt failed to crystallize and was converted to 15 g of the free base in the usual way. The residual oil was chromatographed on a 300 g column of florisil and eluted with a benzene-acetone gradient to give 8 fractions. The second fraction contained most of the pure product (6.1 g), which was converted to the hydrochloride salt with ethereal hydrogen chloride to give 5.3 g of product, m.p. 175°–177° C. Recrystallization from acetone left 2.9 g of hydrochloride salt, m.p., 179.5°–181° C.

Analysis: Calculated for $C_{19}H_{24}NO_2Cl$: C,68.36; H,7.25; N,4.20; Found: C,68.60; H,7.30; N,4.27.

EXAMPLE 29

3-(Phenoxymethyl)-3-piperidinol Hydrochloride [1:1]

A solution of 14.5 g (0.043 mole) of 3-(phenoxymethyl)-1-(phenylmethyl)-3-piperidinol monohydrochloride in 100 ml of 190 ethanol was treated with 1.5 g palladium (II) hydroxide on carbon (20%) and shaken for 6 hours at 70° C. under a hydrogen atmosphere in a Parr apparatus. The catalyst was removed by filtration and the filtrate evaporated under reduced pressure. The solid residue was recrystallized from methanol-ethyl ether to give 6.8 g of hydrochloride salt, m.p. 217°–218° C. (decomposition).

Analysis: Calculated for $C_{12}H_{18}NO_2Cl$: C,59.14; H,7.44; N,5.53; Found: C,58.81; H,7.36; N,5.78.

EXAMPLE 30

4-[(2,6-Dichlorophenoxy)methyl]-1-methyl-4-piperidinol

A suspension of 2.28 g (0.06 mole) of lithium aluminum hydride in 50 ml of dry ethyl ether was stirred under nitrogen at $-5°$ C. and was treated dropwise with a solution of 11 g (ca. 0.03 mole) of a mixture of 4-[(2,6-dichlorophenoxy)methyl]-4-[(ethoxycarbonyl)oxo]piperidine-1-carboxylic acid ethyl ester and 4-[(2,6-dichlorophenoxy)methyl]-4-piperidinol-1-carboxylic acid ethyl ester in 100 ml of dry ethyl ether. No product was detected after 45 min at this temperature by mass spec. analyses. The ice bath was replaced by an ambient temperature bath and the reaction was completed in 20 min. The reaction was terminated by cooling to 0° C. and adding in turn 2.5 ml of water, 2.5 ml of 3N sodium hydroxide and 7 ml of water. After stirring for 30 min the solid salts were removed by filtration and the ether filtrate dried over magnesium sulfate. The magnesium sulfate was removed by filtration and the filtrate was concentrated on a rotary evaporator to give 8 g of a pale orange oil. Repeated triturations with cold isopropyl ether gave 4.6 g of a crude product, m.p. 109°–112° C. Recrystallization from methyl isopropyl ketone gave 1.5 g of large needle-like crystals, m.p. 114°–115° C.

Analysis: Calculated for $C_{13}H_{17}N_1O_2Cl_2$: C,53.81; H,5.91; N,4.83; Found: C,54.00; H,5.85; N,4.85.

EXAMPLE 31

4-[[(1H-2,3-Dihydroinden-5-yl)oxy]methyl]-1-phenylmethyl-4-piperidinol Hydrochloride When in the procedure of Example 16, 5-indanol is substituted for 4-indanol in equal molar amount, the title compound is prepared.

EXAMPLE 32

4-[(2-Ethoxyphenoxy)methyl)]-1-methyl-4-piperidinol

To a solution of 4 g of 4-[(2-ethoxyphenoxy)methyl]-4-hydroxy-1-methyl-1-phenylmethyl-piperidinium iodide in 190 ml of ethanol was added 4.9 g of silver oxide ($Ag_2O$). The reaction mixture was stirred for 20 min and then subjected to catalytic debenzylation conditions using 5% palladium-on-carbon catalyst and hydrogen. The mixture was filtered and the filtrate was concentrated on a rotary evaporator to give 3 g of pale yellow oil. The oil solidified on standing and was recrystallized from ligroin to give 1.3 g of long needle crystals, m.p. 68°–68.5° C.

Analysis: Calculated for $C_{15}H_{23}NO_3$: C,67.90; H,8.74; N,5.28; Found: C,67.82; H,8.79; N,5.26.

Pharmaceutical Compositions

The invention further provides pharmaceutical compositions for administration to living mammals such as humans comprising, as active ingredients, at least one of the compounds according to the invention in association with a pharmaceutical carrier or excipient.

A. Antidepressant and Hypotensive Compositions.

The compounds are presented in a form suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic anc silicic acids, magnesium stearate and polyvinyl pyrrolidone.

For parenteral administration the carrier or excipient can be a sterile, parenterally acceptable liquid, e.g., water, or a parenterally acceptable oil, e.g., arachis oil, contained in ampules. Exemplary of liquid carriers for oral administration are vegetable oils and water.

In compositions for rectal adminstration the carrier can comprise a suppository base, e.g., cocoa butter, or a glyceride.

Although very small quantities of the active materials of the present invention are effective when minor therapy is involved or in cases of administration to subjects having a relatively low body weight, unit dosages are usually from five milligrams or above and preferably 10, 25, 50, or 100 milligrams or even higher, preferably administered three or four times per day depending, of course, upon the emergency of the situation, the compound used, and the particular result desired. Twenty-five to 200 milligrams appear optimum per unit dose or usual broader ranges appear to be about 10 to 500 milligrams per unit dose. Daily dosages usually required should range from about 0.3 to about 20 mg/kg/day, preferably 0.3 to 10 mg/kg for the more active compounds. The active ingredients for the invention may be combined with other compatible pharmacologically active agents. It is only necessary that the active ingredient constitute an effective amount; i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician.

The following formulations are representative for the pharmacologically active compounds of this invention.

1. Capsules

Capsules of 10 mg and 50 mg of active ingredient per capsule are prepared. With the higher amounts of active ingredient, reduction may be made in the amount of lactose.

| Typical blend for encapsulation | 10 mg. Per Capsule | 50 mg. Per Capsule |
| --- | --- | --- |
| Active ingredient, as salt | 10 | 50 |
| Lactose | 259 | 219 |
| Starch | 126 | 126 |
| Magnesium stearate | 4 | 4 |
| Total | 399 | 399 |

Additional capsule formulations preferably contain a higher dosage of active ingredient and are as follows:

| Ingredients | 100 mg. per Capsule | 250 mg. per Capsule | 500 mg. per Capsule |
|---|---|---|---|
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selective active ingredient with lactose, starch, and magnesium stearate and encapsulate the blend.

2. Tablets

A typical formulation for a tablet containing 5.0 mg of active ingredient per tablet follows. The formulation may be used for other strengths of active ingredient by adjustment of weight of dicalcium phosphate.

| | Per Tablet, mg. |
|---|---|
| 1. Active ingredient | 10.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 202.0 |

Uniformly blend 1, 2, 4 and 5. Prepare 3 as a 10 percent paste in water. Granulate the blend with starch paste and pass the wet mass through an 8 mesh screen. The wet granulation is dried and sized through a 12 mesh screen. The dried granules are blended with the calcium stearate and compressed.

3. Injectable—2% sterile solution.

| | Per cc |
|---|---|
| Active ingredient mg. | 20 |
| Preservative, e.g., chlorobutanol, w/vol. percent | 0.5 |
| Water for injection q.s. | |

Prepare solution, clarify by filtration, fill into vials, seals and autoclave.

B. Antiarrhythmia Compositions.

The compounds are presented in a therapeutic composition suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid; e.g., water, or a parenterally acceptable oil; e.g., arachis oil, contained in ampules.

In compositions for rectal administration the carrier can comprise a suppository base; e.g., cocoa butter, or a glyceride.

Advantageously, the compositions are formulated as dosage units, each unit being adapted to supply a fixed dose of active ingredients. Tablets, coated tablets, capsules, ampules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests that the oral dosage effective to correct arrhythmias will be about three times that of the intravenous dosage.

Based on the animal data, allowing for variation in species and severity of cardiac arrhythmia unit dosages containing an amount of compound equivalent to about 1 to about 100 mg/kg of body weight, are contemplated. Based on all of the above considerations, a choice in a range of unit oral dosages for humans of about 10 to about 1000 mg is contemplated, preferably about 10 to 600 mg. Daily dosages of about 30 to 2400 mg are contemplated for humans and obviously several unit dosages forms may be administered at about the same time. However, the scope of the invention is not to be limited by these contemplations due to the uncertainty in transpositions discussed above.

Examples of compositions within the preferred ranges given are as follows:

| Capsules | |
|---|---|
| Ingredients | Per Cap |
| 1. Active ingredient | 10.00 mg |
| 2. Lactose | 146.000 mg |
| 3. Magnesium stearate | 4.000 mg |

Procedure
1. Blend 1, 2 and 3.
2. Mill this blend and blend again.
3. This milled blend is then filled into #1 hard gelatin capsules.

| Tablets (10 mg) | |
|---|---|
| Ingredients | Mg/Tab |
| 1. Active ingredient | 10.0 mg |
| 2. Corn starch | 20.0 mg |
| 3. Kelacid | 20.0 mg |
| 4. Keltose | 20.0 mg |
| 5. Magnesium stearate | 1.3 mg |

| Tablets (50 mg) | |
|---|---|
| Ingredients | Mg/Tab |
| 1. Active ingredient | 50.0 mg |
| 2. Milo starch | 20.0 mg |
| 3. Corn starch | 38.0 mg |
| 4. Lactose | 90.0 mg |
| 5. Calcium stearate | 2.0 mg |
| | 200.0 mg |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
|---|---|
| Ingredients | Per ml. |
| 1. Active ingredient | 1.0 mg |

| -continued | |
|---|---|
| 2. pH 4.0 Buffer solution q.s. to | 1.0 ml |
| Procedure | |
| 1. Dissolve the active ingredient in the buffer solution. | |
| 2. Aseptically filter the solution from Step #1. | |
| 3. The sterile solution is now aseptically filled into sterile ampuls. | |
| 4. The ampuls are sealed under aseptic conditions. | |

| Intramuscular Injection | |
|---|---|
| Ingredients | Per ml |
| 1. Active ingredient | 5.0 mg |
| 2. Isotonic Buffer solution 4.0 q.s. to | 1.0 ml |
| Procedure | |
| 1. Dissolve the active ingredient in the buffer solution. | |
| 2. Aseptically filter the solution from Step #1. | |
| 3. The sterile solution is now aseptically filled into sterile ampuls. | |
| 4. The ampuls are sealed under aseptic conditions. | |

| Suppositories | |
|---|---|
| Ingredients | Per Supp. |
| 1. Active ingredient | 10.0 mg. |
| 2. Polyethylene Glycol 1000 | 1350.0 mg. |
| 3. Polyethylene Glycol 4000 | 450.0 mg. |
| Procedure | |
| 1. Melt 2 and 3 together and stir until uniform. | |
| 2. Dissolve #1 in the molten mass from Step #1 and stir until uniform. | |
| 3. Pour the molten mass from Step #2 into suppository molds and chill. | |
| 4. Remove the suppositories from molds and wrap. | |

Therapeutic compositions having cardiac arrhythmia inhibiting activity in dosage unit form, comprising a pharmaceutical carrier and a cardiac arrhythmia inhibiting amount of a compound of Formula I or a pharmaceutically acceptable acid addition salt thereof are therefore an embodiment of this invention.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What we claim is:

1. A compound selected from aryloxymethylpyrrolidinol and piperidinol compounds of the formula:

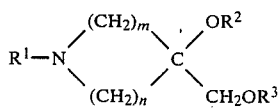

wherein $R^1$ is hydrogen, loweralkyl or phenylloweralkyl, $R^2$ is hydrogen, loweralkyl or acyl; $R^3$ is phenyl, 1-naphthyl, 2-naphthyl, 1H-2,3-dihydroinden-4-yl or 1H-2,3-dihydroinden-5-yl; m is 2 or 3, and n is 1 or 2, with the proviso that m is never 3 when n is 2; and the pharmaceutically acceptable salts thereof.

2. A compound of claim 1 which is 3-phenoxymethyl-1-phenylmethyl-3-pyrrolidinol or a pharmaceutically acceptable salt thereof.

3. A compound of claim 1 which is 4-phenoxymethyl-1-phenylmethyl-4-piperidinol or a pharmaceutically acceptable salt thereof.

4. A compound of claim 1 which is 3-[(2-ethoxy phenoxy)methyl]-1-phenylmethyl-3-pyrrolidinol or a pharmaceutically acceptable salt thereof.

5. A compound of claim 1 which is 4-phenoxymethyl-4-piperidinol or a pharmaceutically acceptable salt thereof.

6. A compound of claim 1 which is 3-[(2-ethoxyphenoxy)methyl]-3-pyrrolidinol or a pharmaceutically acceptable salt thereof.

7. A compound of claim 1 which is 3-[(2-ethoxyphenoxy)methyl]-3-methoxy-1-phenylmethylpyrrolidine or a pharmaceutically acceptable salt thereof.

8. A compound of claim 1 which is 3-[(2-ethoxyphenoxy)methyl]-3-methoxypyrrolidine or a pharmaceutically acceptable salt thereof.

9. A compound of claim 1 which is 3-[(1-naphthalenyloxy)methyl]-1-phenylmethyl-3-pyrrolidinol or a pharmaceutically acceptable salt thereof.

10. A compound of claim 1 which is 3-[(1-naphthalenyloxy)methyl]-3-pyrrolidinol or a pharmaceutically acceptable salt thereof.

11. A compound of claim 1 which is 3-[[(1H-2,3-dihydroinden-4-yl)oxy]methyl]-1-phenylmethyl-3-pyrrolidinol or a pharmaceutically acceptable salt thereof.

12. A compound of claim 1 which is 3-[[(1H-2,3-dihydroinden-4-yl)oxy]methyl]-3-pyrrolidinol or a pharmaceutically acceptable salt thereof.

13. A compound of claim 1 which is 3-ethoxy-3-[(2-ethoxyphenoxy)methyl]pyrrolidine or a pharmaceutically acceptable salt thereof.

14. A compound of claim 1 which is 3-ethoxy-3-[(2-ethoxyphenoxy)methyl]-1-phenylmethylpyrrolidine or a pharmaceutically acceptable salt thereof.

15. A compound of claim 1 which is 4-[(1-naphthalenyloxy)methyl]-4-piperidinol or a pharmaceutically acceptable salt thereof.

16. A compound of claim 1 which is 4-[(1-naphthenyloxy)methyl]-1-phenylmethyl-4-piperidinol or a pharmaceutically acceptable salt thereof.

17. A compound of claim 1 which is 4-[[(1-H-2,3-dihydroinden-4-yl)oxy]methyl]-1-phenylmethyl-4-piperidinol or a pharmaceutically acceptable salt thereof.

18. A compound of claim 1 which is 4-[[(1H-2,3-dihydroinden-4-yl)oxy]methyl]-4-piperidinol or a pharmaceutically acceptable salt thereof.

19. A compound of claim 1 which is 4-[(2-ethoxyphenoxy)methyl]-1-phenylmethyl-4-piperidinol or a pharmaceutically acceptable salt thereof.

20. A compound of claim 1 which is 4-[(2-ethoxyphenoxy)methyl]-4-piperidinol or a pharmaceutically acceptable salt thereof.

21. The compound of claim 1 which is 4-[(2-ethoxyphenoxy)methyl]-4-hydroxy-1-methyl-1-phenylmethyl-piperidinium iodide.

22. The compound of claim 1 which is 4-[(2-ethoxyphenoxy)methyl]-4-methoxy-1-methyl-1-phenylmethyl-piperidinium iodide.

23. A compound of claim 1 which is 4-[(2-ethoxyphenoxy)methyl]-1-methyl-4-piperidinol or a pharmaceutically acceptable salt thereof.

24. A compound of claim 1 which is 3-[(2-ethoxyphenoxy)methyl]-1-phenylmethyl-3-pyrrolidinolacetate (ester) or a pharmaceutically acceptable salt thereof.

25. A compound of claim 1 which is 4-[(4-chlorophenoxy)methyl]-1-phenylmethyl-4-piperidinol or a pharmaceutically acceptable salt thereof.

26. A compound of claim 1 which is 4-[(4-chlorophenoxy)methyl]-4-piperidinol or a pharmaceutically acceptable salt thereof.

27. A compound of claim 1 which is 4-[(2,6-dichlorophenoxy)methyl]-1-phenylmethyl-4-piperidinol or a pharmaceutically acceptable salt thereof.

28. A compound of claim 1 which is 1-methyl-3-(phenoxymethyl)-3-piperidinol or a pharmaceutically acceptable salt thereof.

29. A compound of claim 1 which is 3-(phenoxymethyl)-1-(phenylmethyl)-3-piperidinol or a pharmaceutically acceptable salt thereof.

30. A compound of claim 1 which is 3-(phenoxymethyl)-3-piperidinol or a pharmaceutically acceptable salt thereof.

31. A compound of claim 1 which is 4-[(2,6-dichlorophenoxy)methyl]-1-methyl-4-piperidinol or a pharmaceutically acceptable salt thereof.

32. A pharmaceutical composition comprising a pharmaceutical carrier and a compound effective as an antiarrhythmic, antidepressant or antihypertensive when administered in unit dosage form selected from aryloxymethylpyrrolidinol and piperidinol compounds of the formula:

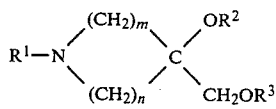

wherein $R^1$ is hydrogen, loweralkyl or phenylloweralkyl; $R^2$ is hydrogen, loweralkyl or acyl; $R^3$ is phenyl, 1-naphthyl, 2-naphthyl, 1H-2,3-dihydroinden-4-yl or 1H-2,3-dihydroinden-5-yl; m is 2 or 3 and n is 1 or 2 with the proviso that m is never 3 when n is 2; and the pharmaceutically acceptable salts thereof.

33. A composition of claim 32 wherein the compound is 4-phenoxymethyl-1-phenylmethyl-4-piperidinol or a pharmaceutically acceptable salt thereof.

34. A composition of claim 32 wherein the compound is 4-phenoxymethyl-4-piperidinol or a pharmaceutically acceptable salt thereof.

35. A composition of claim 32 wherein the compound is 3-[(2-ethoxyphenoxy)methyl]-3-pyrrolidinol or a pharmaceutically acceptable salt thereof.

36. A composition of claim 32 wherein the compound is 3-[(2-ethoxyphenoxy)methyl]-3-methoxypyrrolidine or a pharmaceutically acceptable salt thereof.

37. A composition of claim 32 wherein the compound is 3-[(1-naphthalenyloxy)methyl]-1-phenylethyl-3-pyrrolidinol or a pharmaceutically acceptable salt thereof.

38. A composition of claim 32 wherein the compound is 3-[(1-naphthalenyloxy)methyl-3-pyrrolidinol or a pharmaceutically acceptable salt thereof.

39. A composition of claim 32 wherein the compound is 3-[[(1H-2,3-dihydroinden-4-yl)oxy]methyl]-1-phenylmethyl-3-pyrrolidinol or a pharmaceutically acceptable salt thereof.

40. A composition of claim 32 wherein the compound is 3-[[(1H-2,3-dihydroinden-4-yl)oxy]methyl]-3-pyrrolidinol or a pharmaceutically acceptable salt thereof.

41. A composition of claim 32 wherein the compound is 3-ethoxy-3-[(2-ethoxyphenoxy)methyl]pyrrolidine or a pharmaceutically acceptable salt thereof.

42. A composition of claim 32 wherein the compound is 4-[[(1H-dihydroinden-4-yl)oxy]methyl]-1-phenylmethyl-4-piperidine or a pharmaceutically acceptable salt thereof.

43. A composition of claim 32 wherein the compound is 4-[[(1H-2,3-dihydroinden-4-yl)oxy]methyl]-4-piperidinol or a pharmaceutically acceptable salt thereof.

44. A composition of claim 32 wherein the compound is 1-methyl-3-(phenoxymethyl)-3-piperidinol or a pharmaceutically acceptable salt thereof.

45. A composition of claim 32 wherein the compound is 3-(phenoxymethyl)-1-(phenylmethyl)-3-piperidinol or a pharmaceutically acceptable salt thereof.

46. A composition of claim 32 wherein the compound is 3-(phenoxymethyl)-3-piperidinol or a pharmaceutically acceptable salt thereof.

47. A method of treating cardiac arrhythmia in a patient comprising administering an effective amount of a compound selected from those having the formula:

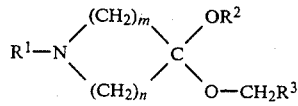

wherein $R^1$ is hydrogen, loweralkyl or phenylloweralkyl; $R^2$ is hydrogen, loweralkyl or acyl; $R^3$ is phenyl, 1-naphthyl, 2-naphthyl, 1H-2,3-dihydroinden-4-yl or 1H-2,3-dihydroinden-5-yl) m is 2 or 3 and n is 1 or 2 with the proviso that m is never 3 when n is 2, and the pharmaceutically acceptable salts thereof.

48. A method of treating hypertension is a patient comprising administering an effective amount of a compound selected from those having the formula:

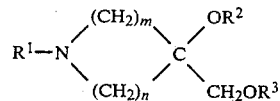

wherein $R^1$ is hydrogen, loweralkyl or phenylloweralkyl; $R^2$ is hydrogen, loweralkyl or acyl; $R^3$ is phenyl, 1-naphthyl, 2-naphthyl, 1H-2,3-dihydroinden-4-yl or 1H-2,3-dihydroinden-5-yl; m is 2 or 3 and n is 1 or 2 with the proviso that m is never 3 when n is 2; and the pharmaceutically acceptable salts thereof.

49. A method of treating depression in a patient comprising administering an effective amount of a compound selected from those having the formula:

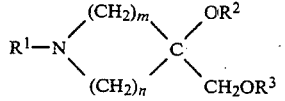

wherein $R^1$ is hydrogen, loweralkyl or phenylloweralkyl; $R^2$ is hydrogen, loweralkyl or acyl; $R^3$ is phenyl, 1-naphthyl, 2-naphthyl, 1H-2,3-dihydroinden-4-yl or 1H-2,3-dihydroinden-5-yl; m is 2 or 3 and n is 1 or 2 with the proviso that m is never 3 when n is 2; and the pharmaceutically acceptable salts thereof.

* * * * *